United States Patent
Chida

(10) Patent No.: US 6,214,605 B1
(45) Date of Patent: Apr. 10, 2001

(54) MICROORGANISM AND A PROCESS FOR PRODUCING POLYOLS BY USING THE SAME

(75) Inventor: Saburo Chida, Kitamoto (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/555,431

(22) PCT Filed: Dec. 21, 1998

(86) PCT No.: PCT/JP98/05773

§ 371 Date: May 30, 2000

§ 102(e) Date: May 30, 2000

(87) PCT Pub. No.: WO99/33953

PCT Pub. Date: Jul. 8, 1999

(30) Foreign Application Priority Data

Dec. 25, 1997 (JP) .................................................. 9-366195

(51) Int. Cl.[7] .............................. C12N 1/14; C12P 7/00; C12P 1/02
(52) U.S. Cl. ...................... 435/254.1; 435/132; 435/171
(58) Field of Search .................................. 435/254.1, 132, 435/171

(56) References Cited

U.S. PATENT DOCUMENTS 4,939,091   7/1990   Sasaki et al. .

FOREIGN PATENT DOCUMENTS

| 63-196298 | 8/1988 | (JP) . |
| 4-635 | 1/1992 | (JP) . |
| 4-11189 | 2/1992 | (JP) . |
| 6-30541 | 4/1994 | (JP) . |
| 6-30592 | 4/1994 | (JP) . |
| 6-30593 | 4/1994 | (JP) . |
| 6-30594 | 4/1994 | (JP) . |
| 9-154589 | 6/1997 | (JP) . |

OTHER PUBLICATIONS

Marina, A.Y., Aoki, Glaucia, M. Pastore and Yong K. Park, "Microbial Transformation of Sucrose and Glucose to Erythritol", *Biotechnology Letters*, vol. 15, No. 4, Apr. 1993, 383–388.

Primary Examiner—Francisco Prats
Assistant Examiner—Susan D. Coe
(74) Attorney, Agent, or Firm—Frishauf, Holtz, Goodman, Langer & Chick, P.C.

(57) ABSTRACT

*Trichosporonoides kounosuensis* 7E-1 (FERM BP-6572) having taxonomical properties different from those of any known species belonging to the genus Trichosporonoides, and having the ability to efficiently produce a polyol such as erythritol.

22 Claims, No Drawings

MICROORGANISM AND A PROCESS FOR PRODUCING POLYOLS BY USING THE SAME

TECHNICAL FIELD

The present invention relates to a novel microorganism and a process for producing polyol by use of the same and in particular to a new strain belonging to the genus Trichosporonoides, that is, *Trichosporonoides kounosuensis* 7E-1 (FERM BP-6572), and a process for producing polyol by use of said strain.

BACKGROUND ART

As microorganisms having been practically used until now in producing polyol particularly erythritol, there are known two microorganisms i.e. *Moniliella tomentosa* var. *pollinis* CBS 461.67 and *Trichosporonoides megachiliensis* SN-G42 (FERM BP-1430) (which is the same as Aureobasidium sp. SN-G42 (FERM P-8940)). For the former, there are known a series of processes for producing polyol by fermentation of saccharides in industrial scale (Japanese Patent Publication Nos. 30591/1994, 30592/1994, 30593/1994 and 30594/1994). For the latter, there is known a novel microorganism having the ability to produce erythritol as well as a process for producing erythritol by fermentation with said microorganism (Japanese Patent Publication Nos. 11189/1992 and 635/1992).

For microorganisms of the genus Trichosporonoides, there is a report of Marina A. Y. Aoki in the State University of Campinas, Brazil, on conversion of glucose and sucrose into erythritol (Biotechnology Letters, Volume 15, No. 4, pp. 383–388, April 1993). According to this report, the rate of conversion of glucose into erythritol is as high as 43.0%, and the rate of conversion of sucrose into erythritol is as high as 37.4%, but the concentration of these saccharides in the culture medium is as low as 10% (W/V), so there is a problem with production in industrial scale.

Further, Ueda et al. in Mitsubishi Chemical Co., Ltd. reported that 5 strains of the genus Trichosporonoides, that is, *Trichosporonoides oedocephalis* CBS 649.66, *Trichosporonoides madida* CBS 240.79, *Trichosporonoides nigrescens* CBS 268.81, *Trichosporonoides spathulata* CBS 241.79, and *Trichosporonoides megachiliensis* CBS 567.85 can form erythritol from glucose (Japanese Patent Laid-Open No. 154589/1997). However, these microorganisms are not necessarily advantageous for large-scale production because the range of their culture temperatures is as narrow as 25 to 37° C. (suitable temperature of 27–35° C.) and a large amount of cooling water is required. Regrettably, it is known that *Trichosporonoides nigrescens* particularly exhibiting the best productivity of 136.0 g/L erythritol does not grow at 37° C. and at a concentration of 50% glucose (infra).

DISCLOSURE OF THE INVENTION

An object of the present invention is to provide a novel microorganism having a high ability to produce polyol, particularly a microorganism producing a large amount of polyol such as erythritol etc. even at relatively high temperatures (35 to 39° C.) and at high sugar levels (20 to 60%).

Another object of the present invention is to provide a process for producing polyol inexpensively by use of this microorganism.

The present inventor made extensive studies to find a novel microorganism having the ability to produce polyol particularly erythritol, and as a result, he found that a novel microorganism separated from a honeycomb solves the aforementioned problem, that is, this microorganism shows good growth at a culture temperature of 35 to 39° C. and at a sugar level of 20 to 60% to produce a large amount of polyol, and the present invention was thereby completed.

That is, the present invention relates to a novel microorganism belonging to the genus Trichosporonoides separated from a honeycomb and in particular to *Trichosporonoides kounosuensis* 7E-1 (FERM BP-6572).

Further, the present invention relates to a process for producing polyol which comprises culturing said microorganism and recovering polyol which mainly contains erythritol, glycerin and ribitol from the culture.

BEST MODE FOR CARRYING OUT THE INVENTION

The novel microorganism of the present invention was separated in the following manner. That is, a honeycomb was cultivated in a medium containing 40% glucose whereby sugar-resistant microorganisms were selected, and the culture temperature was set at 35° C. whereby mesophilic or thermophilic microorganisms were selected. Then, the microorganism separated purely by a conventional microbial separation method was cultured in a medium containing 30% glucose, and measured for the amount of polyol accumulated in the culture, whereby a microorganism having a high ability to produce polyol, specifically *Trichosporonoides kounosuensis* 7E-1, was separated.

This microorganism is internationally deposited as FERM BP-6572 (transferred on Nov. 12, 1998 from Japanese original deposit No. FERM P-16303, originally deposited on Jul. 3, 1997) with the Patent Microbial Deposit Center in the National Institute of Bioscience and Human-Technology, Agency of Industrial Science and Technology of 1–3, Higashi 1-chome, Tsukuba-shi, Ibaraki-ken, Japan.

The mycological properties of *Trichosporonoides kounosuensis* 7E-1 isolated from a honeycomb in Kounosu-shi, Saitama-ken, Japan by the present inventor are described in detail as follows. The mycological properties of *Trichosporonoides kounosuensis* 7E-1 were examined in accordance with "The Yeasts, A Taxonomic Study, Third Revised and Enlarged Edition", edited by N. J. W. Kreger-van Rij Groningen, 1984, published by Elsevier Science Publishers B. V., Amsterdam.

1. The states of growth in medium
1) Microscopical observation
(Culture in YM broth at 25° C. for 3 days)
Size of vegetative cell: 4 to 7.5×4 to 12$\mu$
Shape of vegetative cell: spherical, egg-shaped or oval-shaped
State of vegetative cell: multipolar budding
(Slide culture on potato glucose agar at 25° C. for 7 days)
Blastic conidia: formed
Arthrospores: formed
Pseudomycelia: formed
Hypha: formed
2) Culture in liquid medium (Culture in YM broth at 25° C.)
Growth on the surface: film formation
Turbidity: transparent or slightly turbid
Sedimentation: high
Color of the medium: The medium turns pale brown after about 4-day culture and this color becomes darker, thereafter as the culture proceeds.
3) Agar (Culture on YM agar at 25° C. for 2 weeks)
Growth: good Glossy: absent
Pigment: The colonies, as well as the medium, after culture for 1 week or more turn dark brown.
2. Formation of ascospores
Ascospores are not formed on potato glucose agar, corn meal agar, YM agar, Gorodkowa agar, and acetate medium.
3. Physiological properties

| | |
|---|---|
| requirement for oxygen | aerobic |
| growth temperature | 42° C. |
| optimum growth temperature | 31 to 37° C. |
| pH for growth | 2 to 10.5 |
| optimum pH for growth | 5 to 8 |
| assimilation of KNO$_3$ | positive |
| splitting of fat | negative |
| decomposition of urea | positive |
| liquefaction of gelatin | positive |
| formation of carotenoid | negative |
| formation of organic acids | positive |
| formation of esters | positive |
| formation of starch-like substance | negative |
| requirement for vitamin | positive |
| color reaction with diazonium blue B | positive |
| resistance to osmotic pressure | |
| 10% sodium chloride | positive (growing) |
| 12% sodium chloride | negative (not growing) |
| 60% glucose | positive (growing) |

4. Fermentability of saccharides

| | |
|---|---|
| glucose | positive |
| lactose | negative |
| galactose | positive |
| melibiose | negative |
| raffinose | negative |
| sucrose | positive |
| maltose | positive |
| inulin | negative |
| inositol | negative |

5. Assimilation of carbon compounds

| | |
|---|---|
| D-arabinose | − |
| L-arabinose | + |
| D-ribose | + |
| D-xylose | + |
| D-glucose | + |
| D-mannose | + |
| D-galactose | + |
| L-rhamnose | − |
| D-fructose | + |
| L-sorbose | − |
| maltose | + |
| sucrose | + |
| lactose | − |
| melibiose | − |
| cellobiose | + |
| trehalose | − |
| raffinose | − |
| melezitose | − |
| α-methyl-D-glucoside | − |
| arbtin | + |
| esculin | − |
| salicin | − |
| dextrin | + |
| soluble starch | + |
| inulin | + |
| methanol | − |
| ethanol | + |
| adonitol (ribitol) | − |
| inositol | − |
| erythritol | + |
| D-mannitol | + |
| D-sorbitol | − |
| dulcitol | − |
| xylitol | + |
| glycerin | + |
| DL-lactate | − |
| succinate | + |
| citrate | + |

The properties of the present strain are similar to those of the genus Trichosporon in view of yeast classification according to the above literature (The Yeasts, A Taxonomic Study). However, the properties of the present strain do not agree with those of any species of the genus Trichosporon in respect of color reaction with diazonium blue B, decomposition of urea, fermentation of saccharides, assimilation of KNO$_3$, etc. Due to the length of its blastic conidia, the present strain is classified as the genus Trichosporonoides, on the basis of the classification method described in "The Black Yeasts, II: Moniliella and Allied Genera" edited by G. S. De Hoog in Studies in Mycology No. 19 (1979) (CBS: CENTRAALBUREAU VOOR SCHIMMELCULTURES, The Netherlands).

In view of the species classification method described therein, *Trichosporonoides oedocephalis* CBS 649.66 is different from the present strain in that while the former synchronically forms conidia at the top of a stalk, the present strain does not. Comparison of colony growth on a corn meal agar (culture at 25° C. for 2 weeks) indicated that *Trichosporonoides oedocephalis* showed delayed growth with colonies of 15.5 to 17 mm in diameter. Further, the surface of the colonies was black brown, and formation of aerial hyphae was not observed. On the other hand, the present strain showed vigorous growth with colonies of 31 to 34 mm in diameter, and the surface of the colonies turned grayish white due to vigorous formation of aerial hyphae.

On a potato glucose agar (culture at 25° C. for 2 weeks), *Trichosporonoides oedocephalis* showed moderate growth with colonies of 22 to 22.5 mm in diameter. Further, the surface of the colonies was wrinkled and dark brown in the center and pale brown at the periphery, and thin formation of weak aerial hyphae was observed in places on the surface of the colonies. On the other hand, the present strain showed vigorous growth with colonies of 33 to 34.5 mm in diameter. Further, the surface of the colonies was flat and covered with vigorous aerial hyphae to turn grayish white. On a YM agar (culture at 25° C. for 2 weeks), *Trichosporonoides oedocephalis* showed moderate growth with colonies of 22 to 23 mm in diameter. The surface of the colonies was wrinkled and brown, and the periphery was white to pale brown, and formation of aerial hyphae was observed in places at the periphery of the colonies. On the other hand, the present strain showed vigorous growth with colonies of 32 to 34 mm in diameter. Further, the surface of the colonies was covered with vigorous aerial hyphae to turn grayish white. With respect to assimilation of carbon compounds, *Trichosporonoides oedocephalis* was different from the present strain in that the latter assimilates D-xylose, xylitol and inulin while the former does not.

*Trichosporonoides spathulata* CBS 241.79 forms spoon-shaped hypha stalks, while the present strain does not. Comparison of colony growth in a corn meal agar (culture at 25° C. for 2 weeks) indicated that *Trichosporonoides spathulata* was different from the present strain (supra) in that the former became large with colonies of 50 mm or more in diameter but grew with pale yellowish brown in a very thin form and did not form aerial hyphae. On a potato glucose agar (culture at 25° C. for 2 weeks), *Trichosporonoides spathulata* showed significantly vigorous growth with colonies of 51 to 53 mm in diameter, as compared with growth of the present strain. Further, *Trichosporonoides spathulata* was different from the present strain in that the surface of the former colonies formed wrinkles radially from the center, and the colonies were dark brown in the center and pale brown at the periphery, and on the colonies, grayish white aerial hyphae were formed densely in the center and sparsely towards the periphery, while the surface of colonies of the present strain, as described above, was smooth and free of wrinkles and covered with grayish white well-grown hyphae. On a YM agar (culture at 25° C. for 2 weeks) too, *Trichosporonoides spathulata* showed more vigorous growth with colonies of 44.5 to 47 mm in diameter than the present strain. The surface of the colonies was slightly elevated in the center, wrinkles were formed radially from the center to the periphery, and the whole surface was pure white to form aerial hyphae, while the present strain had grayish white hyphae as described above. With respect to assimilation of carbon compounds, *Trichlosporonoides spathulata* was different from the present strain in that the former assimilates melezitose, raffinose, D-sorbitol, DL-lactate, esculin, and salicin but the latter does not. Further, *Trichosporonoides spathulata* does not require vitamins in the medium and is positive in a test of splitting of tallow, while the present strain requires vitamin and is negative in a test of splitting of tallow.

*Trichosporonoides madida* CBS 240.79 is considerably different from the present strain in that the former hardly forms hypha. Comparison of colony growth on a corn meal agar (culture at 25° C. for 2 weeks) indicated that *Trichosporonoides madida* showed moderate growth with colonies of 23 to 25 mm in diameter and turned dark brown in the center and pale brown at the periphery, and aerial hyphae were not formed. On the other hand, the present strain showed vigorous growth and formed aerial hyphae well, as described above.

On a potato dextrose agar (culture at 25° C. for 2 weeks) too, *Trichosporonoides madida* is different from the present strain. That is, *Trichosporonoides madida* is different from the present strain in that the former shows moderate growth with colonies of 22 to 24.5 mm in diameter, the colonies are black brown, and the surface is elevated to form some lumps, and formation of aerial hyphae is not observed. On a YM agar (culture at 25° C. for 2 weeks) too, *Trichosporonoides madida*, unlike the present strain, showed moderate growth with colonies of 21 to 22 mm in diameter. The surface of the colonies was, unlike the present strain, roughly elevated and dark brown, and the periphery was pale brown. Formation of aerial hyphae was hardly observed. With respect to fermentation of saccharides, *Trichosporonoides madida* is different from the present strain in that the former does not ferment galactose and sucrose. It is reported its fermentation of sucrose is positive in a literature of A. T. Martinez (Studies in Mycology No. 19), but is negative in a literature of G. Douglas and Inglis et al. (G. Douglas Inglis, Lynne Sigler, Mark S. Goettel, TRICHOSPORONOIDES MEGACHILIENSIS, A NEW HYPHOMYCETE ASSOCIATED WITH ALFALFA LEAFCUTTER BEES, WITH NOTES ON TRICHOSPORONOIDES AND MONILIELLA, Mycologia, 84(4), 1992, pp. 555–570), and this agreed with a test result of the present inventor, so its fermentation of sucrose was assumed to be negative. With respect to the assimilation of carbon compounds, *Trichosporonoides madida* is different from the present strain in that the latter assimilates galactose and inulin, while the former does not.

In view of the classification method described in the literature of G. Douglas and Inglis et al. (supra), *Trichosporonoides nigrescens* CBS 268.81 is different from the present strain in that the former neither grows at 37° C. nor ferments sucrose. With respect to assimilation of carbon sources, *Trichosporonoides nigrescens* is different from the present strain in that the former does not assimilate L-arabinose and D-xylose but assimilates D-sorbitol. Comparison of colony growth on a corn meal agar (culture at 25° C. for 2 weeks) indicated that *Trichosporonoides nigrescens* was different from the present strain in that the former showed weak growth with colonies of 9 to 9.5 mm in diameter. The colonies were dark black brown in the center and pale brown at the periphery, and formation of aerial hyphae was not observed. On the other hand, the present strain showed vigorous growth, and aerial hyphae were formed well, as described above.

On a potato glucose agar (culture at 25° C. for 2 weeks) too, *Trichosporonoides nigrescens* is different from the present strain. That is, *Trichosporonoides nigrescens*, unlike the present strain, showed moderate growth with colonies of 17.5 to 19 mm in diameter, and the colonies were black brown and the surface was elevated to form some lumps, and formation of aerial hyphae was not observed. These characteristics are different from those of the present strain. On a YM agar (culture at 25° C. for 2 weeks) too, *Trichosporonoides nigrescens* showed considerably delayed growth with colonies of 13 to 14.5 mm in diameter, as compared with growth of the present strain. The surface of colonies was dark brown, and was elevated to form some lumps, and formation of aerial hyphae was not observed. These characteristics are different from those of the present strain.

Similarly, in view of the classification method described in the literature of G. Douglas and Inglis et al. (supra), *Trichosporonoides australiense* (Ramirez, 1989) is different from the present strain in that the former ferments lactate but does not assimilate L-arabinose and D-xylose, as opposed to the latter which does not ferment lactose but assimilates L-arabinose and D-xylose. Further, *Trichosporonoides australiense* is different from the present strain in that the former is poor in sugar resistance and does not grow on a medium containing 50% glucose, but the latter grows well even on a medium containing 60% glucose. Furthermore, *Trichosporonoides australiense* does not produce urease, so it is negative both in decomposition of urea and in color reaction with diazonium blue B, whereas the present strain is positive in both.

*Trichosporonoides megachiliensis* CBS 567.85 is different from the present strain in that the former assimilates neither nitrates nor L-arabinose, D-xylose, xylitol and inulin. Comparison of colony growth on a corn meal agar (culture at 25° C. for 2 weeks) indicated that *Trichosporonoides megachiliensis* showed growth with colonies of 28 to 29.5 mm in diameter, similar to growth of the present strain, but the surface of colonies was flat and grew with black brown in a thin form, and aerial hyphae formed were very thin and weak. On the other hand, the aerial hyphae of the present strain were formed well so that the brown color of the colony base could not be seen, and the color of the colonies was thereby made grayish white.

On a potato glucose agar (culture at 25° C. for 2 weeks) too, *Trichosporonoides megachiliensis* is different from the present strain. That is, *Trichosporonoides megachiliensis* showed growth with colonies of 25 to 27 mm in diameter, similar to the growth of the present strain. However, the colonies of *Trichosporonoides megachiliensis*, unlike those of the present strain, hardly formed aerial hyphae and the surface thereof was flat and black brown. Further, the edges of colonies in the periphery, unlike the colonies of the present strain, elongated radially into the medium in a unique form similar to a burr. On a YM agar (culture at 25° C. for 2 weeks), *Trichosporonoides megachiliensis* showed vigorous growth with colonies of 29.8 to 30.5 mm in diameter, almost similar to growth of the present strain. However, formation of aerial hyphae was limited to a part of the surface of colonies e.g. about half of the surface, as opposed to the present strain which formed aerial hyphae over the whole surface of colonies.

Accordingly, the present strain is a new species which though belonging to the genus Trichosporonoides, differs from the previously reported *Trichosporonoides oedocephalis, Trichosporonoides spathulata, Trichosporonoides madida, Trichosporonoides nigrescens, Trichosporonoides australiense*, and *Trichosporonoides megachiliensis*. The present inventor named this new species *Trichosporonoids kounosuensis*. Besides the above novel strain, any mutant thereof obtained from the present new species naturally or artificially by such treatments as ultraviolet irradiation and mutagenesis agent also falls under the scope of the present invention, as long as it has an ability to produce polyol.

The culture of the present strain is conducted under aerobic culture conditions in a liquid medium containing a carbon source, a nitrogen source, inorganic salts etc.

The carbon source includes saccharides such as glucose, fructose, sucrose etc., and a starch-saccharified liquor containing these saccharides, and sugars such as sweet potato syrup, beet syrup etc. The concentration of the saccharides in the medium is 20 to 60%, preferably 30 to 50%.

The nitrogen source includes nitrogenous compounds utilizable by the microorganism, such as yeast extract, peptone, malt extract, corn steep liquor, ammonia water, ammonium salts, urea, nitrates etc.

Phosphates, magnesium salts, calcium salts, potassium salts, iron salts, manganese salts etc. are suitably used as the inorganic salts.

Culturing is conducted usually at a culture temperature of 25 to 40° C., preferably 35 to 39° C. for 3 to 10 days during which polyol mainly containing erythritol, glycerin and ribitol is accumulated in the culture medium. The total yield of polyol (yield relative to sugar) is 35 to 45% in the case of sugar concentration in the medium of 20 to 50 W/V %, and for example 43.7% in the case of glucose concentration in the medium of 30 W/V %.

The method of recovering the polyol accumulated in the medium may be effected in any method known in the art, for example by removing the microbial cells by filtration or centrifugation, followed by purification of the polyol by a suitable combination of treatment with ion-exchange resins, absorption chromatography, extraction with solvent, crystallization by concentration under cooling, and so on. The polyol may be purified by decoloration with active carbon or recrystallization generally used for removing impurities.

Hereinafter, the examples of the present invention are described in detail by reference to the Examples, which are not intended to limit the present invention.

EXAMPLE 1

Comparison of the Amounts of Polyol Produced at Different Culture Temperatures

*Trichosporonoids kounosuensis* 7E-1 (FERM BP-6572) was inoculated into a yeast extract medium (30 W/V % glucose, 1 W/V % yeast extract) and cultivated at 35° C. for 3 days under shaking. Then, the resulting culture liquid was inoculated at a concentration of 2% based on the amount of the medium into the same yeast extract medium previously introduced into an L-shaped culture tube, and the microorganism was cultured for 6 days at 60 rpm at a temperature in the range of 15.9 to 46.2° C. in a shake temperature gradient incubator (Model TN-2148, Advantec Toyo K. K.). Then, the amounts of polyol (g/L) produced at different temperatures were compared.

The amount of polyol produced and the amount of glucose remaining in the culture were determined by quantification in high performance liquid chromatography (HPLC) (Model RID-6A, Shimadzu Corporation). For comparison, the growth of the microorganism in the culture was also expressed in terms of culture turbidity (absorbance at 660 nm×degree of dilution of the culture). The results are shown in Table 1.

TABLE 1

| Culture Temp. (° C.) | Polyol Production (g/L) | | | | |
|---|---|---|---|---|---|
| | turbidity | glucose | erythritol | glycerin | ribitol |
| 15.9 | 42.7 | 216.0 | 13.8 | 11.2 | 2.7 |
| 18.3 | 44.9 | 186.1 | 20.7 | 13.3 | 5.4 |
| 21.0 | 53.1 | 160.8 | 29.5 | 16.2 | 5.2 |
| 23.5 | 50.1 | 123.7 | 35.1 | 16.2 | 6.8 |
| 26.1 | 49.6 | 85.3 | 44.2 | 20.4 | 12.9 |
| 28.7 | 64.9 | 37.3 | 68.3 | 38.0 | 31.2 |
| 31.3 | 77.7 | 5.4 | 82.0 | 41.9 | 33.8 |
| 33.9 | 101.9 | 0 | 92.5 | 35.1 | 28.6 |
| 36.7 | 84.5 | 0 | 85.9 | 31.6 | 12.7 |
| 39.4 | 56.5 | 0 | 111.0 | 17.8 | 10.5 |
| 42.7 | 5.5 | 278.8 | 5.0 | 6.1 | 0 |
| 46.2 | 3.8 | 296.7 | 3.0 | 0 | 0 |

EXAMPLE 2

Glucose Concentration and Polyol Production

*Trichosporonoids kounosuensis* 7E-1 (FERM BP-6572) was inoculated into a yeast extract medium (30 W/V % glucose, 1 W/V % yeast extract) and cultured at 35° C. for 3 days under shaking. Then, the resulting culture liquid was inoculated at a concentration of 2% based on the amount of the medium into a sugar concentration test medium previously introduced into an Erlenmeyer flask, that is, a yeast extract medium (C/N ratio in the yeast extract medium was constant) prepared at a glucose concentration of 20, 30, 40 or 50 W/V %, and the microorganism was cultured at 220 rpm at 35° C. The culture was continued until the glucose in the medium was almost consumed (115 to 157 hours). The amount of polyol produced in the culture was determined by quantification in HPLC (Model RID-6A, Shimadzu Corporation). The results are shown in Table 2. The yield relative to glucose in the table is the yield of total polyol relative to consumed glucose.

TABLE 2

| Glucose Conc. (W/V %) | Culture Time | Polyol (g/L) | | | Total Polyol (yield relative to Glucose) |
|---|---|---|---|---|---|
| | | erythritol | glycerin | ribitol | |
| 20 | 115 | 67.7 | 12.1 | 6.7 | 86.5(43.9%) |
| 30 | 115 | 91.5 | 25.3 | 14.4 | 131.2(43.7%) |
| 40 | 141 | 115.2 | 42.5 | 16.1 | 173.7(43.4%) |
| 50 | 157 | 97.4 | 56.4 | 13.2 | 167.0(35.9%) |

EXAMPLE 3

Sucrose Concentration and Polyol Production

*Trichosporonoides kounosuensis* 7E-1 (FERM BP-6572) was inoculated into a yeast extract medium (30 W/V % glucose, 1 W/V % yeast extract) and cultured at 35° C. for 3 days under shaking. Then, the resulting culture was inoculated at a concentration of 2% based on the amount of the medium into a sucrose concentration test medium previously introduced into an Erlenmeyer flask, that is, a sucrose yeast extract medium (C/N ratio in the yeast extract medium was constant) prepared at a sucrose concentration of 20, 30, 40 or 50 W/V %, and the microorganism was cultured at 220 rpm at 35° C. The culture was continued until the sucrose in the medium was almost consumed (115 to 157 hours). The amount of polyol produced in the culture was determined by quantification in HPLC (Model RID-6A, Shimadzu Corporation). The results are shown in Table 3. The yield relative to sucrose in the table is the yield of total polyol relative to consumed sucrose.

TABLE 3

| Sucrose Conc. (W/V %) | Culture Time | Polyol (g/L) erythritol | glycerin | ribitol | Total Polyol (yield relative to Glucose) |
|---|---|---|---|---|---|
| 20 | 115 | 64.4 | 2.7 | 5.4 | 72.5(36.7%) |
| 30 | 115 | 99.2 | 9.8 | 8.0 | 117.0(39.3%) |
| 40 | 141 | 142.9 | 10.5 | 5.9 | 159.3(40.2%) |
| 50 | 157 | 157.4 | 14.9 | 4.2 | 176.5(35.5%) |

EXAMPLE 4

Fructose Concentration and Polyol Production

*Trichosporonoides kounosuensis* 7E-1 (FERM BP-6572) was inoculated into a yeast extract medium (30 W/V % glucose, 1 W/V % yeast extract) and cultured at 35° C. for 3 days under shaking. Then, the resulting culture was inoculated at a concentration of 2% based on the amount of the medium into a sugar concentration test medium previously introduced into an Erlenmeyer flask, that is, a fructose yeast extract medium (C/N ratio in the yeast extract medium was constant) prepared at a fructose concentration of 40 W/V %, and the microorganism was cultured at 220 rpm at 35° C. for 10 days. As a result, 192.1 (g/L) polyol (i.e. erythritol, glycerin and ribitol in total) was produced in the culture medium.

EXAMPLE 5

*Trichosporonoides kounosuensis* 7E-1 (FERM BP-6572) was inoculated into a yeast extract medium (30 W/V % glucose, 1 W/V % yeast extract) and cultured at 35° C. for 3 days under shaking. Then, the resulting culture was inoculated at a concentration of 2% based on the amount of the medium into a sugar concentration test medium previously introduced into an Erlenmeyer flask, that is, a yeast extract medium (C/N ratio in the yeast extract medium was constant) prepared at a glucose concentration of 30 or 40 W/V %, and the microorganism was cultured at 220 rpm at 38.5° C. The culture was continued until the glucose in the medium was almost consumed (113 or 143 hours). The amount of polyol produced in the culture was determined by quantification in HPLC (Model RID-6A, Shimadzu Corporation). The result indicated that the total yield of polyol was 43.7% in the 30% glucose medium, and the total yield of polyol was 44.0% in the 40% glucose medium.

INDUSTRIAL APPLICABILITY

The novel microorganism of the present invention has taxonomical properties different from those of any known species of the genus Trichosporonoides, and is a useful microorganism having a high ability to produce polyol such as erythritol. Further, polyol such as erythritol can be produced efficiently by use of said microorganism.

What is claimed is:

1. *Trichosporonoides kounosuensis* 7E-1 (FERM BP-6572) which has an ability of accumulating polyol in the culture medium by culturing in a medium containing sugar.

2. A process for producing polyol, which comprises culturing *Trichosporonoides kounosuensis* 7E-1 (FERM BP-6572) in a medium at a sugar concentration of 20 to 60% and recovering polyol accumulated in the medium.

3. The process for producing polyol according to claim 2, wherein the medium is a medium containing glucose, fructose or sucrose as main components.

4. The process for producing polyol according to claim 2 wherein the polyol is a polyol containing erythritol, glycerin and ribitol as main components.

5. The process for producing polyol according to claim 2, wherein the concentration of the sugar in the medium is 20 to 60% and the culturing is carried out at a culture temperature of 25 to 40° C.

6. The process for producing polyol according to claim 2, wherein the concentration of the sugar in the medium is 30 to 50% and the culturing is carried out at a culture temperature of 35 to 39° C.

7. The process for producing polyol according to claim 2, wherein the polyol accumulated in the medium has a yield of 35% or more relative to saccharide.

8. The process, for producing polyol according to claim 3, wherein the polyol is a polyol containing erythritol, glycerin and ribitol as main components.

9. The process for producing polyol according to claim 3, wherein the concentration of the sugar in the medium is 20 to 60% and the culturing is carried out at a culture temperature of 25 to 40° C.

10. The process for producing polyol according to claim 4, wherein the concentration of the sugar in the medium is 20 to 60% and the culturing is carried out at a culture temperature of 25 to 40° C.

11. The process for producing polyol according to claim 8, wherein the concentration of the sugar in the medium is 20 to 60% and the culturing is carried out at a culture temperature of 25 to 40° C.

12. The process for producing polyol according to claim 3, wherein the concentration of the sugar in the medium is 30 to 50% and the culturing is carried out at a culture temperature of 35 to 39° C.

13. The process for producing polyol according to claim 4, wherein the concentration of the sugar in the medium is 30 to 50% and the culturing is carried out at a culture temperature of 35 to 39° C.

14. The process for producing polyol according to claim 8, wherein the concentration of the sugar in the medium is 30 to 50% and the culturing is carried out at a culture temperature of 35 to 39° C.

15. The process for producing polyol according to claim 11, wherein the concentration of the sugar in the medium is 30 to 50% and the culturing is carried out at a culture temperature of 35 to 39° C.

16. The process for producing polyol according to claim 3, wherein the polyol accumulated in the medium has a yield of 35% or more relative to saccharide.

17. The process for producing polyol according to claim 4, wherein the polyol accumulated in the medium has a yield of 35% or more relative to saccharide.

18. The process for producing polyol according to claim 5, wherein the polyol accumulated in the medium has a yield of 35% or more relative to saccharide.

19. The process for producing polyol according to claim 6, wherein the polyol accumulated in the medium has a yield of 35% or more relative to saccharide.

20. The process for producing polyol according to claim 8, wherein the polyol accumulated in the medium has a yield of 35% or more relative to saccharide.

21. The process for producing polyol according to claim 11, wherein the polyol accumulated in the medium has a yield of 35% or more relative to saccharide.

22. The process for producing polyol according to claim 15, wherein the polyol accumulated in the medium has a yield of 35% or more relative to saccharide.

* * * * *

UNITED STATES PATENT AND TRADEMARK OFFICE
CERTIFICATE OF CORRECTION

PATENT NO. : 6,214,605 B1
DATED : April 10, 2001
INVENTOR(S) : Saburo Chida

It is certified that error appears in the above-identified patent and that said Letters Patent is hereby corrected as shown below:

Title page,
Item [56], Referencs Cited, FOREIGN PATENT DOCUMENTS, replace "6-30541" with -- 6-30591 --.

Signed and Sealed this

Thirtieth Day of November, 2004

JON W. DUDAS
*Director of the United States Patent and Trademark Office*